United States Patent
McLean, Jr.

Patent Number: 6,161,436
Date of Patent: Dec. 19, 2000

[54] SHOE FOR ULTRASONICALLY INSPECTING CRANKSHAFT FILLETS

[75] Inventor: Hugh B. McLean, Jr., Lafayette, Ind.

[73] Assignee: Caterpillar Inc., Peoria, Ill.

[21] Appl. No.: 09/326,158

[22] Filed: Jun. 4, 1999

[51] Int. Cl.$^7$ .................................................. G01N 29/00
[52] U.S. Cl. .......................................... 73/632; 73/644
[58] Field of Search .......................... 73/622, 625, 628, 73/637, 640, 644, 632, 641, 633

[56] References Cited

U.S. PATENT DOCUMENTS

| | | | |
|---|---|---|---|
| 3,169,393 | 2/1965 | Stebbins | 73/67.9 |
| 3,958,451 | 5/1976 | Richardson | 73/67.8 S |
| 4,065,960 | 1/1978 | Grabendorfer et al. | 73/627 |
| 4,099,418 | 7/1978 | Bennett et al. | 73/622 |
| 4,258,573 | 3/1981 | Fontaine | 73/621 |
| 4,474,064 | 10/1984 | Naruse et al. | 73/622 |
| 4,487,072 | 12/1984 | Livingston | 73/622 |
| 4,532,808 | 8/1985 | Wentzell et al. | 73/640 |
| 4,562,737 | 1/1986 | Davies | 73/622 |
| 4,596,953 | 6/1986 | Nagasaka et al. | 324/242 |
| 4,709,582 | 12/1987 | Besanceney | 73/622 |
| 4,712,428 | 12/1987 | Ishii et al. | 73/644 |
| 4,807,476 | 2/1989 | Cook et al. | 73/620 |
| 4,843,884 | 7/1989 | House et al. | 73/622 |
| 5,203,869 | 4/1993 | Bashyam | 73/640 |
| 5,279,160 | 1/1994 | Koch | 73/643 |
| 5,343,750 | 9/1994 | Bashyam | 73/635 |
| 5,402,682 | 4/1995 | Patzke | 73/622 |
| 5,431,054 | 7/1995 | Reeves et al. | 73/612 |
| 5,535,628 | 7/1996 | Rutherford | 73/622 |
| 5,681,996 | 10/1997 | White | 73/622 |
| 5,698,787 | 12/1997 | Parzuchowski et al. | 73/643 |
| 6,019,001 | 2/2000 | Schreiner et al. | 73/640 |

*Primary Examiner*—Richard A. Moller
*Attorney, Agent, or Firm*—Fred J. Baehr

[57] ABSTRACT

A shoe for ultrasonically inspecting an area beneath the fillets of a crankshaft and the area adjacent each side of the fillets for flaws in the highly stressed fillet area, the shoe comprising a planar surface and a cylindrical surface disposed at a right angle thereto with a toroidal surface forming an smooth transition therebetween and mating with surfaces on the crankshaft, the shoe houses three transducer oriented toward the centerline of the cylindrical surface and disposed to generally form angles of 22.5°, 45° and 67.5° with the centerline of the cylindrical surface, the transducer oriented at 45° is generally one half the radius of the fillet so it does not produce any surface waves, the other two transducers are generally twice as large and oriented so the surface waves produced do not converge under the central transducer, whereby the ultrasonic inspection can detect small inclusions and defects with adequate signal to noise ratio and near surface resolution covering the entire fillet and a portion of the journal surface of the crankshaft adjacent to the fillet.

10 Claims, 2 Drawing Sheets

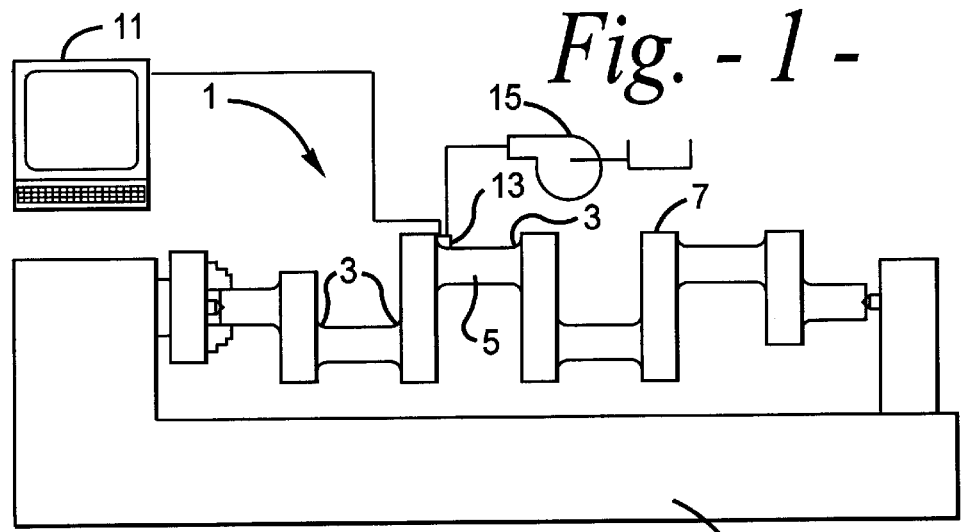
Fig. -1-
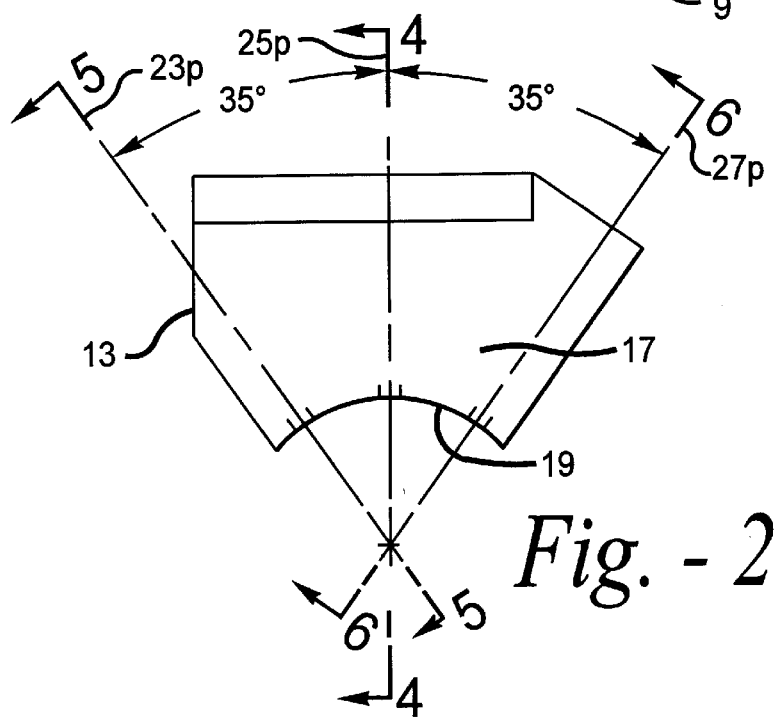
Fig. -2-
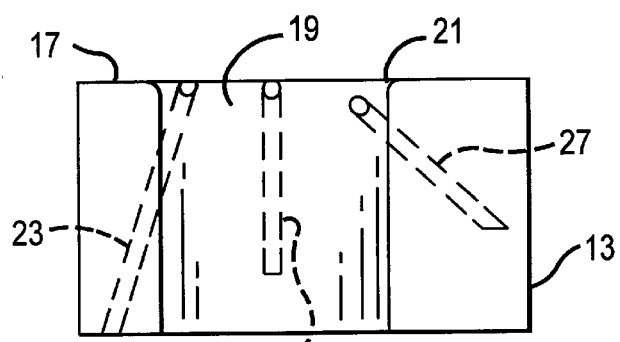
Fig. -3-

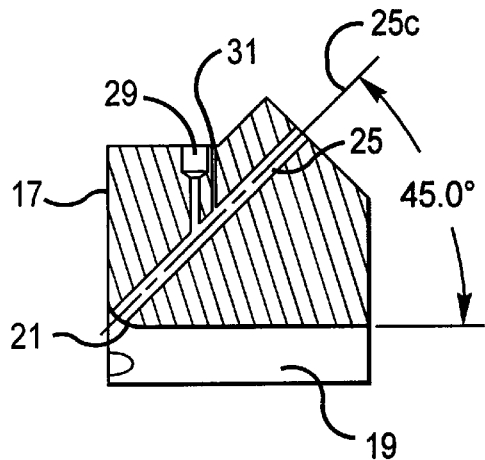
Fig. - 4 -
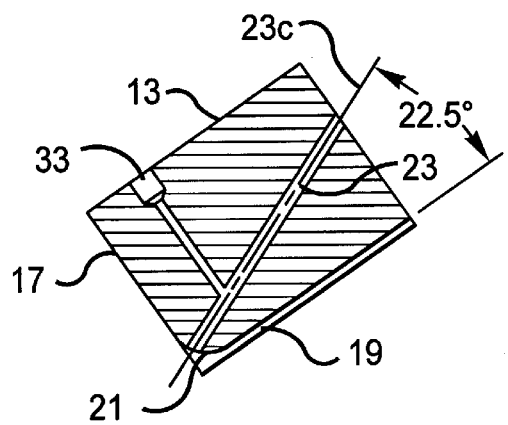
Fig. - 5 -
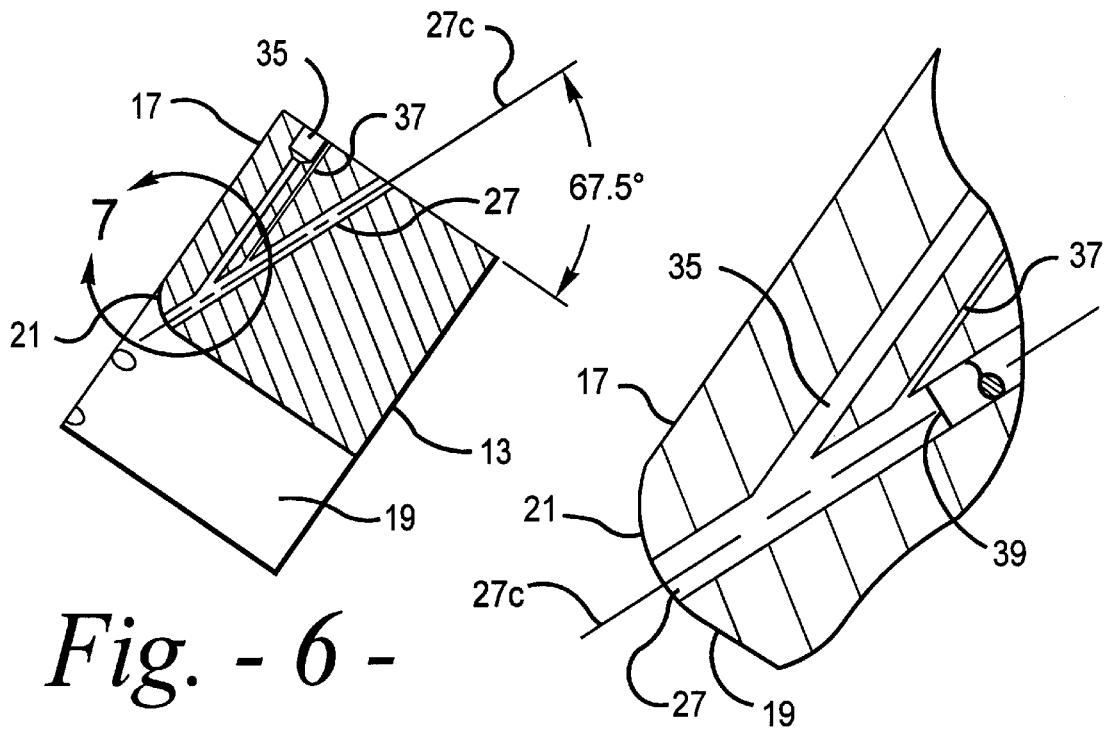
Fig. - 6 -
Fig. - 7 -

SHOE FOR ULTRASONICALLY INSPECTING CRANKSHAFT FILLETS

TECHNICAL FIELD

The invention relates to ultrasonic inspection of a crankshaft fillet and more particularly to a shoe that places the right size transducers in proper positions to inspect the fillets for subsurface defects.

BACKGROUND ART

The subsurface area adjacent the fillets of a crankshaft are highly stressed so that undetected subsurface defects and inclusions in the metal structure in the area beneath the fillets and the adjacent subsurface area will cause premature failure of the crankshaft. Inspection of the subsurface volume of fillet material has been impractical due to limited depth of material under inspection and the low inspection sensitivity.

DISCLOSURE OF THE INVENTION

Among the objects of the invention may be noted the provision of a shoe for housing a plurality of transducers to adequately ultrasonically inspect the highly stressed area of a crankshaft beneath the fillets and the area adjacent thereto for defects that could cause premature failure of the crankshaft.

In general, a shoe for ultrasonically inspecting the area beneath the fillets on a crankshaft having a journal surface and a fillet on each end thereof, when made in accordance with this invention, comprises a generally cylindrical surface which generally mates with a portion of the journal surface of the crankshaft, a generally toroidal surface which generally mates with a portion of the fillets and a planar surface intersecting the toroidal surface. The shoe also comprises three spaced apart through holes. Each of the through holes extends form a portion of the toroidal surface. A centrally disposed hole receives a transducer having a diameter that will produce no surface waves when radiating the fillet with ultrasonic waves. The other two holes are disposed outboard of the central hole. Each of the outboard holes receive a transducer that has a larger diameter than the transducer in the central hole and are oriented so that when radiating the fillet with ultrasonic waves, the surface waves generated do not converge beneath the central through hole, whereby the ultrasonic inspection can detect small inclusions and defects with adequate signal to noise ratio covering the entire fillet and a portion of the straight length and provide linear sensitivity with depth and near the surface resolution.

BRIEF DESCRIPTION OF THE DRAWINGS

The invention as set forth in the claims will become more apparent by reading the following detailed description in conjunction with the accompanying drawings, wherein like reference numerals refer to like parts throughout the drawings and in which:

FIG. 1 is a schematic view of a system for ultrasonically inspecting the area beneath the fillets adjacent the journals of a crankshaft;

FIG. 2 is an elevational view of a shoe for ultrasonically inspecting the area beneath the fillets on the crankshaft;

FIG. 3 is a bottom view of the shoe;

FIG. 4 is a sectional view taken on line IV—IV of FIG. 2;

FIG. 5 is a sectional view taken on line V—V of FIG. 2;

FIG. 6 is a sectional view taken on line VI—VI of FIG. 2; and

FIG. 7 is an enlarged partial sectional view showing the location of a transducer disposed in the through hole shown in FIG. 6.

BEST MODE FOR CARRYING OUT THE INVENTION

Referring now to the drawings in detail and in particular to FIG. 1, there is shown an ultra sonic inspection system 1 for ultrasonically inspecting the area beneath fillets 3 disposed adjacent journals 5 of a crankshaft 7. The crankshaft 7 is rotatably disposed in a lathe 9 or other means for rotating the crankshaft 7. An ultrasonic instrument 11 comprises a personal computer based multi-channel device such as a Krautkramer Branson Inc. model USPC-2100 comprising three channels with each channel having independent gain, time controlled gain, range, interface gates, and interface triggered inspection gates. A shoe 13 having three transducers (not shown) disposed therein. One of the transducers is electrically connected to each of the three channels. A coupling fluid supply system 15 supplies coupling fluid to the shoe 13. The coupling fluid transmits the ultrasonic waves between the transducers and the crankshaft 7 and from the crankshaft 7 back to the transducers.

Referring now in detail to FIGS. 2 and 3, the shoe 13 is shown to comprise a front planar surface 17, a portion of a cylindrical surface 19 that generally mates with the surface of the journals 5 on the crankshaft 7 and a portion of a toroidal surface 21 that generally mates with the fillets 3. The toroidal surface 21 forms a smooth transition between the planar and cylindrical surfaces 17 and 19. Three through holes 23, 25 and 27 are so disposed in the shoe 13 that they each provide an opening in at least a portion of the toroidal surface 21. The holes 23, 25 and 27 have centerlines 23c, 25c and 27c respectively. The centerlines 23c, 25c and 27c are disposed, respectively, in three radial planes 23p, 25p and 27p that pass through a centerline of the cylindrical surface 19. The planes 23p and 25p are disposed form an angle of 35° therebetween and the planes 25p and 27p are disposed form an angle of 35° therebetween.

Referring now to FIG. 4 in detail, the centerline 25c of the through hole 25 is centrally disposed in the shoe 13 and forms an angle of 45° with a line on the cylindrical surface 19 that is parallel to the centerline of the cylindrical surface 19. The through hole 25 has a diameter that is generally about one half the radius of the fillet 3 or smaller. An opening on one end of the through hole 25 is generally centered in the toroidal surface 21 so that the ultrasonic waves produced by a transducer (not shown) disposed therein does not produce any surface waves, only longitudinal and shear waves. Larger transducers so disposed produced large false indications. A coupling fluid supply port 29 is disposed in fluid communication with the through hole 25 to flood the portion of the hole 25 between the transducer and the crankshaft 7 with coupling fluid to transmit ultrasonic waves between the area beneath the fillet 3 and the transducer. One or more weep holes 31 are also disposed in fluid communication with the hole 25 to remove air bubbles that would interfere with the transmission of ultrasonic waves through the coupling fluid.

Referring now to FIG. 5 in detail, the centerline 23c of the through hole 23 is shown to form an angle of 22.5° with a line on the cylindrical surface 19 that is parallel to the centerline of the cylindrical surface 19. The through hole 23 has a diameter that is generally about twice the radius of the fillet 3. The opening of the through hole 23 is disposed in the planar surface 17 and in the toroidal surface 21 so that ultrasonic waves from a transducer (not shown) disposed therein radiates into the area beneath the fillet 3 and into an area adjacent the fillet 3 to detect flaws beneath the fillet 3 and the area adjacent thereto. A coupling fluid inlet port 33 is disposed in fluid communication with the through hole 23 to supply coupling fluid thereto. One or more weep holes (not shown) are also disposed in fluid communication with the through hole 23 to remove air bubbles from the coupling fluid.

Referring now to FIG. 6 in detail the centerline 27c of the through hole 27 forms an angle of 67.5° with a line parallel to the centerline of the cylindrical surface 19. The through hole 27 has a diameter that is generally about twice the radius of the fillet 3. The opening of the through hole 27 is disposed in the cylindrical surface 19 and in the toroidal surface 21 so that ultrasonic waves from a transducer (not shown) disposed therein radiates into the area beneath the fillet 3 and into an area adjacent the fillet 3 to detect flaws beneath the fillet 3 and the area adjacent thereto. A coupling fluid port 35 is disposed in fluid communication with the through hole 27 to supply coupling fluid thereto. One or more weep holes 37 are also disposed in fluid communication with the coupling fluid port 35 to remove air bubbles from the coupling fluid.

Referring now to FIG. 7 in detail there is shown a portion of a transducer 39 disposed in the through hole 27 beyond the supply port 35 and weep hole 37. The portion of the hole 27 between the transducer 39 and the crankshaft (not shown) is flooded with coupling fluid, preferably water.

Typically the transducers 39 are generally about 25 millimeters from the opening of the through holes 23, 25 and 27 so the near field of the transducer 39 is in the coupling fluid this combined with the size of the transducers 39 relative to the radius of the fillet and the orientation of the through holes 23, 25 and 27 to provide adequate signal to noise ratio covering the entire fillet and a portion of the straight length and near the surface resolution.

A calibration block (not shown) with 1.5 millimeter diameter flat bottom holes at depths of 3 and 10 millimeters is utilized to calibrate the ultrasonic instrument 11 and the transducers 39 in each of the through holes 23, 25 and 27.

To inspect the area beneath the fillets 3 and the area adjacent thereto the shoe 13 is placed on the journal portion 5 of the crankshaft 7 adjacent the fillet 3. The crankshaft 7 is rotated by the lathe 9 and the coupling fluid supply system floods the portions of the through holes 23, 25 and 27 between the transducers 39 and the crankshaft 7 with coupling fluid. The ultrasonic instrument is turned on to ultrasonically inspect the area beneath the fillet 3 and the area adjacent thereto. The ultrasonic inspection system 1 provides adequate signal to noise ratio covering the entire fillet and a portion of the straight length and near the surface resolution to detect defects and inclusions below the surface which may cause premature failure in this highly stressed portion of the crankshaft 7.

While the preferred embodiments described herein set forth the best mode to practice this invention, presently contemplated by the inventors, numerous modifications and adaptations of this invention will be apparent to others of ordinary skill in the art. Therefore, the embodiments are to be considered as illustrative and exemplary and it is understood that the claims are intended to cover such modifications and adaptations as they are considered to be within the spirit and scope of this invention.

Industrial Applicability

An ultrasonic inspection system that can detect small inclusions and small defects in structure of the metal with adequate signal to noise ratio covering the entire fillet and a portion of the straight length and near the surface resolution during the manufacturing process can prevent premature failure of crankshafts and save thousands of dollars in engine repair and downtime.

What is claimed is:

1. A shoe for ultrasonically inspecting the area beneath the fillets on a crankshaft having a journal surface and a fillet on each end thereof, the shoe comprising a generally cylindrical surface which generally mates with a portion of the journal surface of the crankshaft, a generally toroidal surface portion which generally mates with a portion of the fillets and a planar surface intersecting the toroidal surface, the shoe having three spaced apart through holes each of which extends from a portion of the toroidal surface, a centrally disposed hole having a diameter that receives a transducer having a diameter that will produce no surface waves when radiating the fillet with ultrasonic waves and the other holes are disposed outboard of the central hole, each outboard through hole having a diameter that receives an outboard transducer having a larger diameter than the transducer in the central hole and the outboard transducers are oriented so that when radiating the fillet with ultrasonic waves, the surface waves generated by the outboard transducers do not converge in the area beneath the central through hole, whereby the ultrasonic inspection can detect small inclusions and defects with adequate signal to noise ratio and near surface resolution covering the entire fillet and a portion of the journal surface adjacent to the fillet.

2. The shoe as set forth in claim 1, wherein the diameter of the central through hole and the transducer disposed therein is generally less than half the diameter of the fillet.

3. The shoe as set forth in claim 2, wherein the diameter of the two outboard through holes and the transducers disposed therein is generally twice the diameter of the central through hole and the transducer disposed therein.

4. The shoe as set forth in claim 3, wherein the three through holes have center lines that when extended beyond the shoe generally intersect a centerline of the cylindrical surface and the center line of each the holes is generally disposed in a radial plane that passes through the center line of the cylindrical surface and the planes containing the centerlines of the outboard through holes each form an angle of about 35° with the central plane.

5. The shoe as set forth in claim 4, comprising a coupling fluid port in fluid communication with each of the through holes to flood a space disposed between the associated transducer and the fillet with a coupling fluid.

6. The shoe as set forth in claim 5, comprising at least one weep hole in fluid communication with each of the through holes to remove all air bubbles in the coupling fluid between the associated transducer and the fillet.

7. The shoe as set forth in claim 4, wherein the centerline of the central hole generally forms an angle of about 45° with a centerline of the cylindrical surface.

8. The shoe as set forth in claim 7, wherein the centerline of one of the outboard through holes generally forms an angle of about 22.5° with the centerline of the cylindrical surface and the centerline of the other outboard through hole generally forms an angle of about 67.5° with the centerline of the cylindrical surface.

9. The shoe as set forth in claim 8, wherein the outboard through hole that forms an angle of about 22.5° with the centerline of the cylindrical surface has an opening partially disposed in the toroidal surface and partially disposed in the planar surface and the outboard through hole that forms an angle of 67.5° with the centerline of the cylindrical surface has an opening partially disposed in the toroidal surface and partially disposed in the cylindrical surface.

10. The shoe as set forth in claim 9, wherein each transducer has individual gain, time control gain, range, interface gates, and interfaced triggered inspection gates.

* * * * *